United States Patent [19]
Lake

[11] Patent Number: 5,951,284
[45] Date of Patent: Sep. 14, 1999

[54] INTRAORAL INSTRUMENT

[76] Inventor: James A. Lake, 4750 N. Jupiter #221, Garland, Tex. 75044

[21] Appl. No.: 09/037,418

[22] Filed: Mar. 10, 1998

[51] Int. Cl.[6] ........................................................ A61C 1/00
[52] U.S. Cl. .................................................. 433/31; 433/9
[58] Field of Search ................................. 433/31, 30, 91, 433/93, 80

[56] References Cited

U.S. PATENT DOCUMENTS

| | | | |
|---|---|---|---|
| 1,925,981 | 9/1933 | Hopkings | 433/31 |
| 1,989,162 | 1/1935 | Barr | 433/31 |
| 2,176,620 | 10/1939 | Beam | 32/69 |
| 2,720,702 | 10/1955 | Freedman | 433/31 |
| 2,834,109 | 5/1958 | O'Hara | 32/69 |
| 2,907,110 | 10/1959 | O'Hara | 32/69 |
| 2,984,009 | 5/1961 | Codoni | 32/69 |
| 3,006,073 | 10/1961 | McCarter | 32/69 |
| 3,027,644 | 4/1962 | Piscitelli | 32/69 |
| 3,102,338 | 9/1963 | Warriner | 433/31 |
| 3,164,904 | 1/1965 | Barnes | 32/69 |
| 3,250,005 | 5/1966 | White | 32/27 |
| 3,352,305 | 11/1967 | Freedman | 128/173.1 |
| 3,543,405 | 12/1970 | Banhart | 433/31 |
| 3,614,415 | 10/1971 | Edelman | 240/2.18 |
| 3,638,013 | 1/1972 | Keller | 240/41.15 |
| 3,849,889 | 11/1974 | Rosander | 32/22 |
| 3,928,916 | 12/1975 | Hansson | 32/69 |
| 3,969,824 | 7/1976 | Widen et al. | 32/69 |
| 3,986,266 | 10/1976 | Vellender | 32/69 |
| 4,279,594 | 7/1981 | Rigutto | 433/31 |
| 4,512,635 | 4/1985 | Melde | 350/640 |
| 4,629,425 | 12/1986 | Detsch | 433/31 |
| 4,790,751 | 12/1988 | Reinhardt | 433/29 |
| 4,872,837 | 10/1989 | Issalene et al. | 433/29 |
| 4,925,391 | 5/1990 | Berlin | 433/31 |
| 5,139,421 | 8/1992 | Verderber | 433/31 |
| 5,449,290 | 9/1995 | Reitz | 433/31 |
| 5,813,856 | 9/1998 | Lee | 433/31 |

*Primary Examiner*—Gene Mancene
*Assistant Examiner*—Pedro PhiloGene
*Attorney, Agent, or Firm*—Dennis T. Griggs

[57] ABSTRACT

A double-sided mirror and irrigation instrument for intraoral application has an in-line finger operated valve for selectively controlling flow of air, water or a mixture of air and water through an annular supply passage for cleaning the mirror surfaces and objects in the oral cavity. An annular suction passage extends from the mirror assembly through an extension tube for draining liquids from the patient's mouth. The mirror assembly is illuminated by light transmitted through a quartz rod that is enclosed within a central supply conduit.

19 Claims, 4 Drawing Sheets

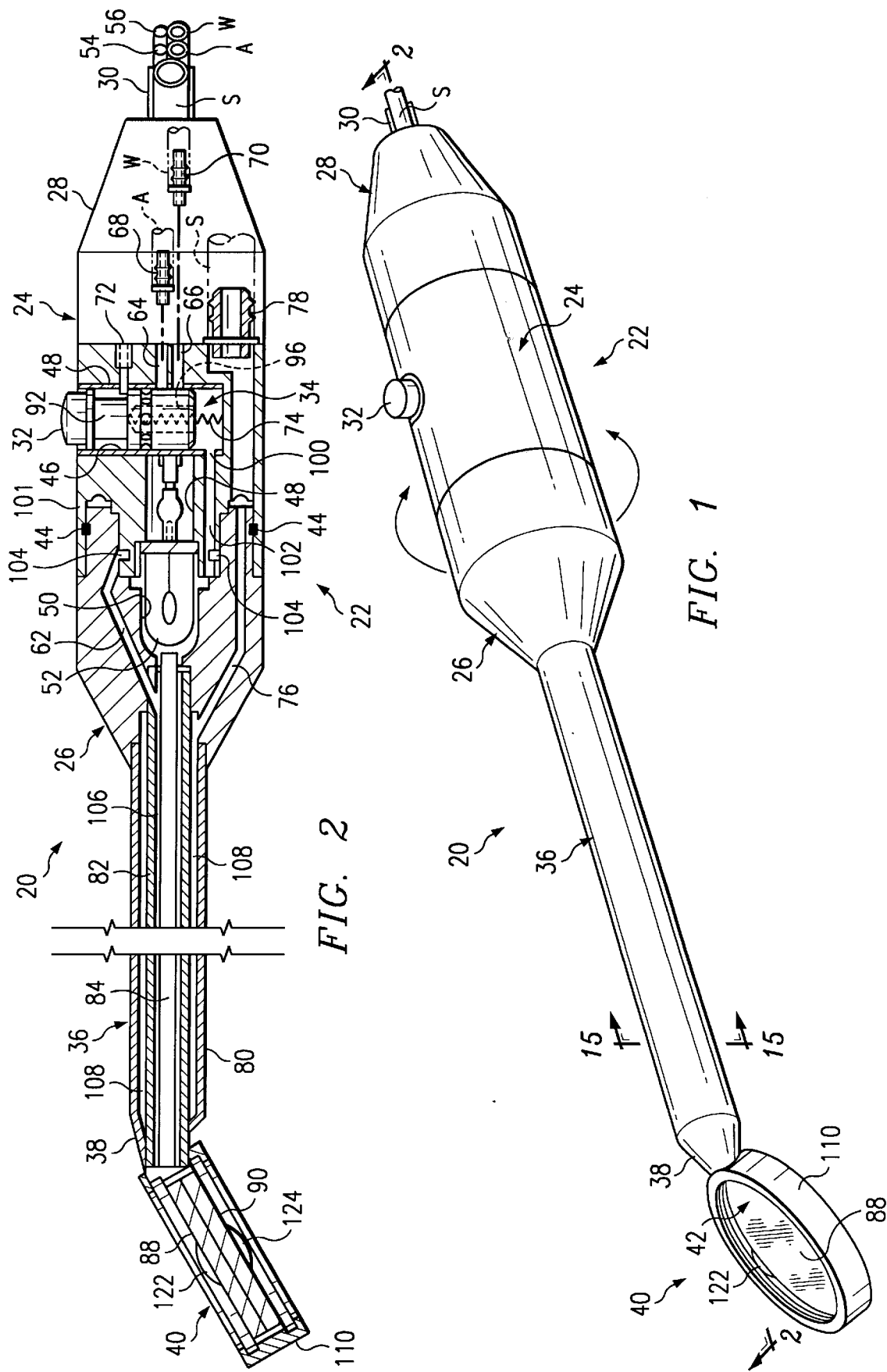

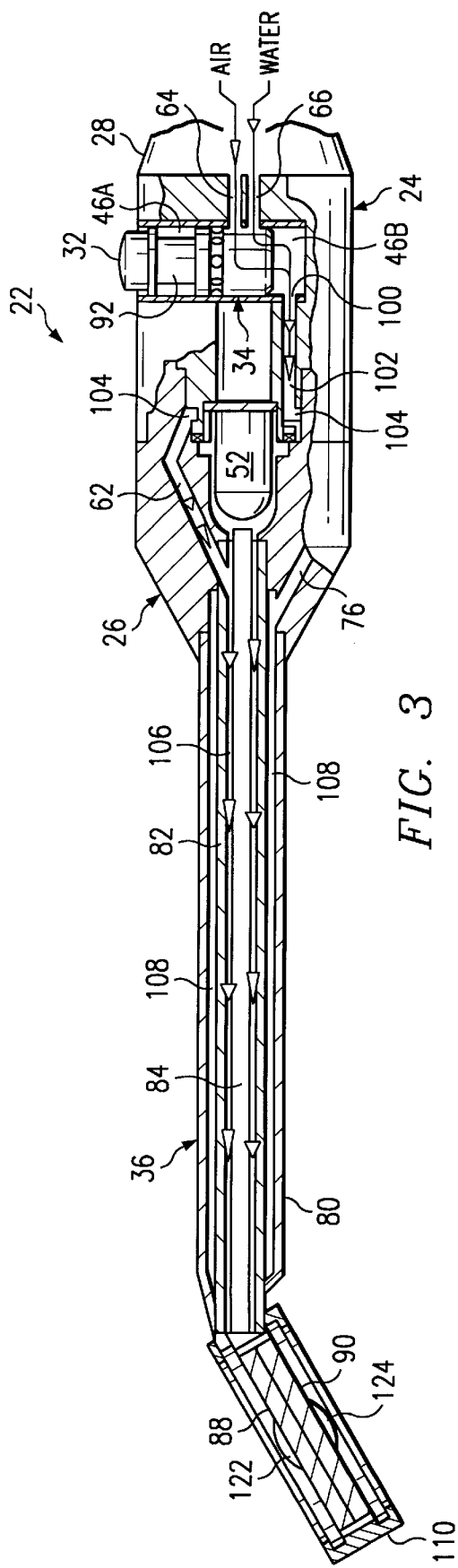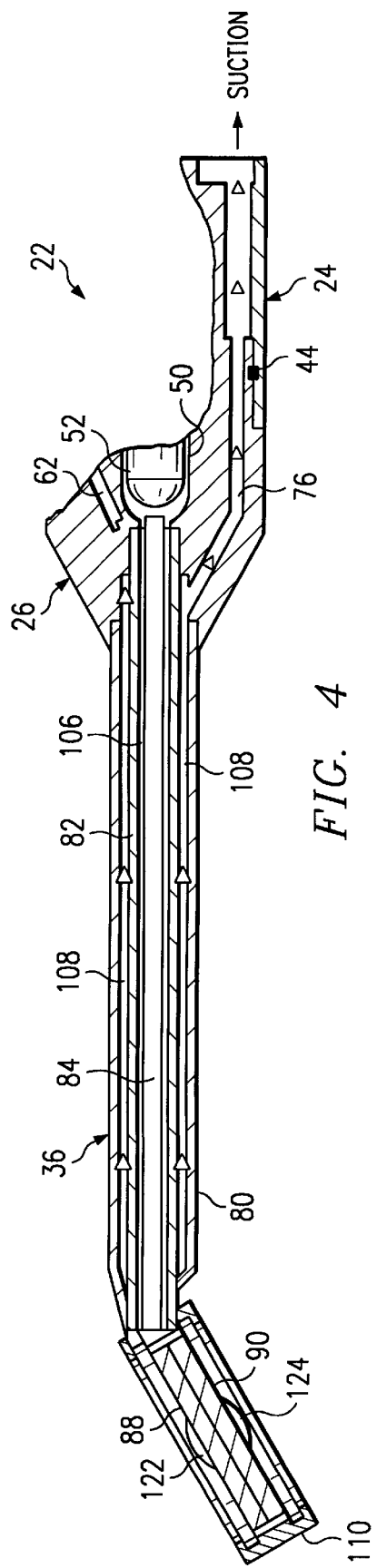
FIG. 3
FIG. 4

INTRAORAL INSTRUMENT

BACKGROUND OF THE INVENTION

This invention relates generally to dental instruments, and in particular to a swivelable, self-cleaning, illuminated, intraoral mirror instrument having an in-line finger operated valve for controlling the flow and mixture of air and water across the mirror.

Dental mirrors have long been used to assist dentists in performing diagnostic and treatment procedures. Conventional instruments generally include a narrow handle carrying a small mirror arranged at an oblique angle to the handle so that it can be inserted into the patient's mouth for viewing the patient's teeth and gums. During use, the mirror surface may be obscured by condensation, spray from a high speed drill, tooth detritus and treatment material that collects on the mirror surface. During the course of conventional dental procedures, the mirror surface must be cleared frequently by removing the instrument from the patient's mouth and then rinsing the mirror surface. Thus, the problem of maintaining the mirror surface clear has long been recognized and various means have been proposed for solving the problem. Moreover, various proposals have been set forth for illuminating the patient's mouth during dental procedures.

DESCRIPTION OF THE PRIOR ART

One conventional approach for clearing a dental mirror without removing it from the patient's mouth is to direct a stream of air, water or a spray of air and water onto the mirror surface. A limitation of this technique is that the mirror surface is typically located a substantial distance from the air/water source. Thus the air, water, or mixture of air and water is projected toward the mirror with little or no control over the manner in which it is applied against the mirror surface.

Conventional intraoral instruments that direct air, water or a mixture of air and water onto the mirror surface employ separate actuators for controlling the flow of air and water to the mirror surface, resulting in an inefficient operation. Moreover, such instruments do not provide suction for removing water and other debris from the mirror surface to assist in the cleaning process.

Moreover, conventional intraoral instruments do not provide for rotation of the mirror surface relative to the handle. Consequently, the dentist must rotate the entire dental instrument to reposition the mirror surface. Due to the air, water, electrical conductors and fiber optics conductors that are routed through the handle, such instruments have a relatively large diameter making manipulation difficult.

Accordingly, there is a need for an improved intraoral instrument for effectively and efficiently spraying air, water or a mixture of air and water across the mirror surface as well as providing illumination and suction flow from the mirror surface, while enabling easy manipulation of the mirror for efficient performance of dental diagnostic and treatment procedures.

SUMMARY OF THE INVENTION

The intraoral instrument of the present invention includes a cylindrical handle containing air, water and electric supply lines and a suction discharge line. An extension tube is mounted for rotation on the handle and supports a double-sided mirror assembly. A quartz rod extends through the extension tube to conduct light from a lamp in the handle to the mirror. An annular supply passage formed between the quartz tube and an inner supply conduit extends through the extension tube to conduct air and water or a mixture of air and water from the air and water supply lines to the mirror assembly for washing and drying the mirror surfaces. A manually operable valve assembly mounted within the handle selectively controls the flow of air, water or a mixture of air and water through the supply passage. An annular suction passage formed between the inner flow conduit and the extension tube conveys water, saliva and debris from the mirror assembly to the suction flow line.

According to one aspect of the invention, the valve assembly includes a flow control valve and an actuator movable by finger depression from an OFF position to a first operating position which permits the passage of air only from the air supply line. When the flow control valve is further depressed to a second operating position, the valve assembly permits the passage of both air and water from the air and water supply lines. When the flow control valve is depressed still further to a third operating position, the flow control valve permits the passage of water only.

According to another aspect of the invention, the mirror assembly includes a double-sided mirror having multiple discharge slots formed in peripheral edge portions of the mirror that are in flow communication with the supply passage to provide controlled washing and drying of the mirror surfaces. In addition, the mirror housing includes multiple slots disposed around the mirrors that are in communication with the suction passage for removing water, saliva and debris from the mirror and the patient's mouth.

According to yet another aspect of the invention, the extension tube is rotatably coupled to a tapered end of the handle for easy manipulation of the mirror without requiring rotation of the entire instrument.

One advantage of the present invention is that it permits single finger control of the flow of air only, spray of air and water, and flow of water only across the mirror surfaces of the instrument through the use of a single push actuator.

Another advantage of the double-sided embodiment of the present invention is that it permits the operator to selectively work from the top side of the mirror or the bottom side of the mirror and selectively control the flow of water and air to the reflective mirror surfaces to make more efficient use of the mirror.

Another advantage of the present invention is that air, water or a mixture of air and water is discharged directly onto the mirror surface through slots disposed on the periphery of the mirror surfaces to provide thorough clearing and drying of the mirror surfaces.

Still another advantage of the invention is that it provides simultaneous direct spray and suction removal of rinse water, treatment material, drilling debris and saliva from the patient's mouth and the mirror surface.

BRIEF DESCRIPTION OF THE DRAWINGS

Referring now to the drawings in which like reference numerals indicate corresponding elements throughout the several views:

FIG. 1 is a general perspective view of an intraoral instrument constructed according to the present invention;

FIG. 2 is a side sectional view taken approximately along the line 2—2 of FIG. 1;

FIG. 3 is a partial sectional view of the intraoral instrument showing the air and water flow passageways in greater detail;

FIG. 4 is a sectional view thereof, partly broken away, showing the suction flow passageway in greater detail;

DETAILED DESCRIPTION OF THE INVENTION

Figure 5:
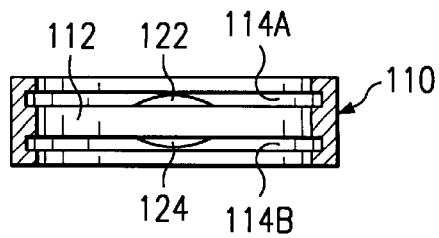
FIG. 5 is a side sectional view of the mirror housing.
Figure 6:
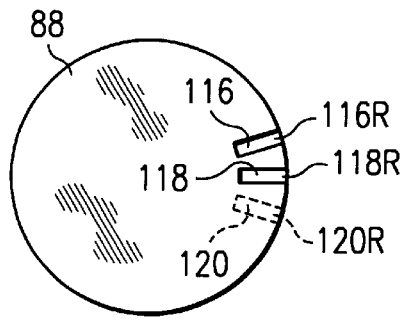
FIG. 6 is a top plan view of the mirror assembly shown in FIG. 2.
Figure 7:
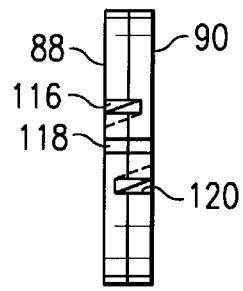
FIG. 7 is a right side elevational view of the double-sided mirror assembly of FIG. 6.
Figure 8:
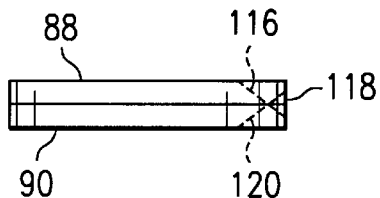
FIG. 8 is a left side elevational view of the double-sided mirror assembly of FIG. 6.

In the description which follows, like parts are marked throughout the specification and drawings with the same reference numerals, respectively. The drawing figures are not necessarily drawn to scale and the proportions of certain parts have been exaggerated for purposes of clarity.

Referring to FIGS. 1 and 2, an intraoral instrument 20 constructed according to the preferred embodiment of the present invention includes a handle 22 having a cylindrical valve housing 24 and front and rear tapered handle end portions 26 and 28, respectively. The front tapered end 26 is rotatably coupled to the cylindrical valve housing 24. The handle 22 is enclosed within a knurled elastomer covering (not illustrated) to improve the gripping surface. The rear tapered end 28 is removably attached to the cylindrical valve housing 24 and preferably tapers to an opening through which a bundle 30 containing air, water, electric supply lines and a suction flow line are routed. A grommet (not shown) or other strain relief device is fitted within the opening to relieve stress on the bundle 30. A thumb/finger activated valve actuator 32 for controlling the operating position of an air/water valve assembly 34 extends through the cylindrical valve housing 24 substantially perpendicular to its cylindrical axis.

The front tapered end 26 of the handle 22 is joined to a tubular extension member 36 which extends along a longitudinal axis that is substantially coaxial with the longitudinal axis of the handle 22. The tubular extension member 36 is rigidly attached to the tapered front end 26 and is rotatable therewith. A tapered coupling collar 38 is formed on the distal end of the tubular extension member 36. A mirror assembly 40 containing a double sided mirror 42 is rigidly attached to the tapered coupling collar 38.

Referring now to FIG. 2, the front tapered end 26 is rotatably coupled within a cylindrical socket 43 (FIG. 14) formed the cylindrical housing 24 and is sealed by an O-ring 44. A cavity 50 is formed in the tapered handle end portion 26 for receiving a lamp 52. The handle 22 encloses the air/water valve assembly 34, a lamp 52, electrical power leads 54, 56, a compressed air supply conduit A, a water supply conduit W, and a suction conduit S.

The valve assembly 34 is disposed for vertical reciprocal movement within a valve chamber 46. The valve chamber 46 is formed in the handle 22 in a substantially transverse relationship with the longitudinal axis of the handle. The valve chamber 46 may be machined in a solid portion of the handle 22, but is preferably provided by a cylindrical insert 48. The valve assembly includes a cylindrical valve body portion 34A that forms a movable partition between an upper chamber 46A and a lower chamber 46B.

Figure 9:
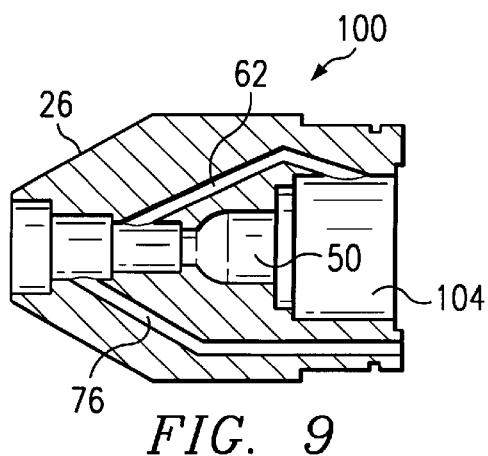
FIG. 9 is a sectional view of the front tapered section of the instrument body.
Figure 13:
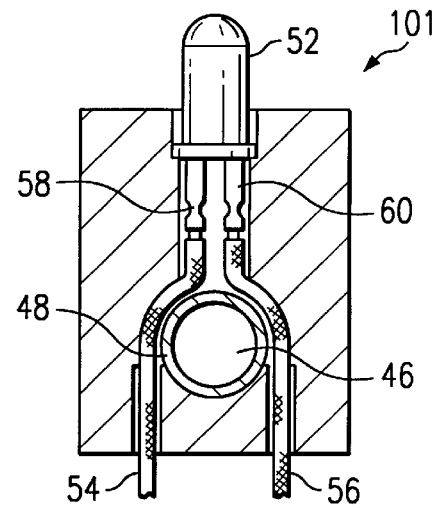
FIG. 13 is a top plan view of a lamp installed in the intraoral instrument shown in FIG. 2.

Referring now to FIGS. 2, 9 and 13, the lamp 52 is mounted with its optical axis extending substantially coaxial with the longitudinal axis of the handle. As shown in FIG. 13, the lamp 52 is electrically connected to power leads 54, 56 which are routed around the valve chamber 46 and out through the bundle 30. The electrical leads 54, 56 are crimped or soldered to electrical connector pins 58 and 60, respectively.

A supply passage 62 (FIG. 2 and FIG. 9) is formed through the front tapered end 26 and opens at one end into a collector annulus 104. An air supply conduit 64 and a water supply conduit 66 couple the valve chamber 46 to the water supply line W and air supply line A through an air nipple coupling 68 and a water nipple coupling 70 that are coupled to the air supply conduit 64 and the water supply conduit 66, respectively. A valve retaining screw 72, located in the upper valve chamber 46A and accessible by removing the tapered rear end 28, provides a limit stop for restricting upward movement of the valve assembly 34 beyond the OFF position.

Figure 11:
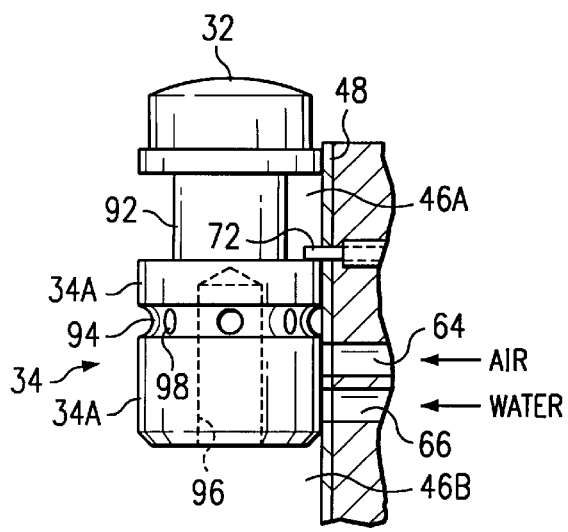
FIG. 11 is an elevational view, partly in section, showing the valve actuator in the OFF position.

Referring again to FIG. 2, the valve assembly 34 is biased by a spring 74 for upward movement against the retaining screw 72 in the OFF position so that the valve body 34 blocks the flow of water and air through the air and water supply conduits 64 and 66, respectively, as shown in FIG. 11. A suction passage 76 is formed through the front tapered end 26 and is coupled to a return flow nipple 78.

Figure 10:
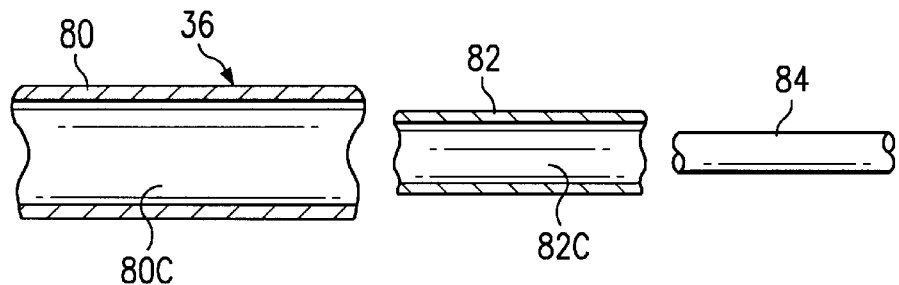
FIG. 10 is an exploded view, partly in section, of the outer tube, the inner tube, and the quartz rod shown in FIG. 2.
Figure 15:
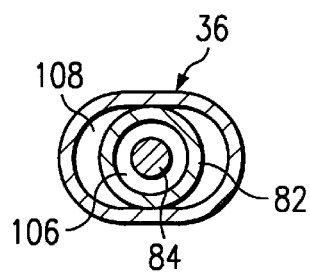

The tubular extension member 36 is formed by an outer oval tubular housing 80 having a central flow passage 80C. A tubular inner flow conduit 82 is disposed coaxially substantially within the central flow passage 80C. A quartz rod 84 is disposed coaxially within the inner tube 82 and is coextensive therewith, as shown in FIGS. 10 and 15.

As shown in FIGS. 2, 3 and 4, an annular supply flow passage 106 is formed between the inner flow tube 82 and the quartz rod 84 and is coupled to the supply passage 62 for conducting water and/or air to the mirror assembly 40. An annular return flow passage 108 is formed in the annulus between the outer tube 36 and the inner flow conduit 82. The return flow passage 108 conducts water, air, saliva and debris from the mirror assembly 40 through the suction flow passage 76 to the nipple 78 and the suction flow line S.

The mirror assembly 40 includes a first single sided mirror 88 stack-mounted on a second single sided mirror 90, thereby forming a double-sided (top and bottom) mirror assembly. The quartz rod 84 is aligned with the lamp 52 and conducts light through the extension tube 36 to illuminate the mirrors 88, 90 of the double-sided mirror assembly 40.

Figure 12:
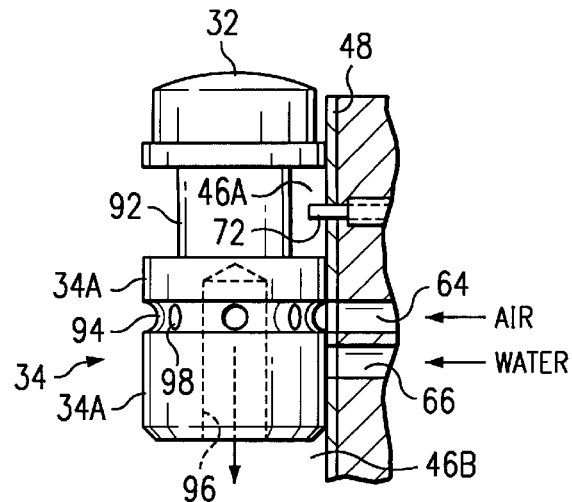
FIG. 12 is an elevational view, partly in section, showing the valve actuator of the present invention in the AIR ONLY position.

Referring now to FIGS. 2, 11 and 12, the push actuator 32 of the flow control valve assembly is attached to an extension shaft 92 that is connected to the valve body 34A. The valve body 34A is intersected radially by an annular groove 94 which provides a passageway for air or water when aligned with either the air supply conduit 64 or the water supply conduit 66, respectively.

The valve body portion 34A is also intersected by a longitudinal bore 96 in which the bias spring 74 is received.

The valve body 34A is further intersected by radial bores 98 which couple the annular groove 94 in fluid communication with the longitudinal spring bore 96 and the lower valve chamber 46B. The annular groove 94 allows either air only, a mixture of water and air, or water only to flow through the radial bores 98 into the spring bore 96. From the spring bore 96, the air and/or water flows into the lower valve chamber 46B, through an outlet port 100, into the collector annulus 104, through the supply passage 62, and then through the annular supply passage 106 for discharge directly onto the mirror surfaces 88, 90.

As shown in FIG. 11, the annular groove 94 is alignable first with the air supply passage 64 as the valve actuator 32 is depressed to an AIR position so that only compressed air is permitted to flow through the radial bores 98 into the spring bore 96 in proportion to the amount of the area exposed by registration of the annular groove 94 with the air supply port 64. Further depression of the valve actuator 32 to an AIR & WATER position (FIG. 14) aligns the annular groove 94 with both the air supply port 64 and the water supply port 66 to allow compressed air and water to flow simultaneously through the radial bores 98 into the spring bore 96. Still further depression of the valve actuator 32 to a WATER position aligns the annular groove 94 with only the water supply passage 66 thus allowing only water to flow through the radial bores 98 and into the spring bore 96.

Figure 14:
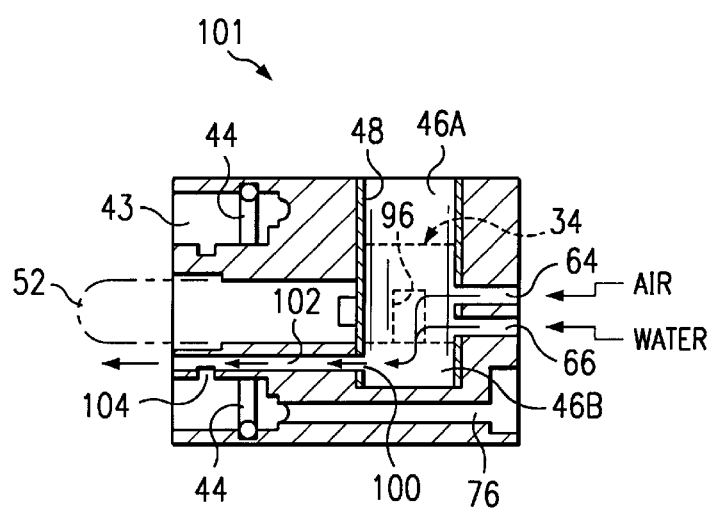
FIG. 14 is a partial sectional view detailing the valve chamber of the intraoral instrument shown in FIG. 2; and, FIG. 15 is a sectional view taken along the line 15—15 of FIG. 1.

Referring now to FIGS. 2, 13 and 14, a distribution manifold 101 conducts the flow of air, water or a mixture of air and water through the lower valve chamber 46B, through the supply bore 102, into the collector annulus 104, through the supply flow passage 62, where it then flows through the extension supply annulus 106, for discharge onto the mirror assembly 40 at the distal end of the tubular extension member 36.

Reference is now made to FIG. 4 which shows a partial side sectional view of the suction flow path. An annular return flow passage 108 formed between the outer extension tube 80 and the inner supply conduit 82 conducts suction flow from the mirror assembly 40 through the extension tube 36 to the extraction passage 76 for discharge through the nipple 78 into the suction return flow line S.

Referring now to FIGS. 5, 6, 7 and 8, the mirror assembly 40 is shown in detail. The mirror assembly 40 includes a cylindrical housing 110 having a mirror chamber 112 and annular flow grooves 114A, 114B. Preferably, the single-sided mirrors 88, 90 are bonded together by a deposit of silicon rubber adhesive. The mirrors 88 and 90 include slots 116, 118 and 120 intersecting their peripheral edge portions so that air and water may be discharged from the supply annular flow passage 62 transversely across the mirrors 88 and 90.

By manual rotation of the double mirror assembly within the mirror housing, the edge slots 116, 118 and 120 are separately alignable in flow communication with the annular supply passage 106 to direct fluid flow transversely across the top mirror 88 only (edge slot 116), across both mirrors 88, 90 (edge slot 118), or across the bottom mirror 90 only (edge slot 120). Rinse water is admitted through suction ports 122, 124 formed in the mirror housing 110 and is drawn into the suction annular flow passage 62 and conveyed through the return flow passage 76 and the nipple 78 to the suction return line S.

In the preferred embodiment, the slots have sloping surfaces that are covered by reflective coatings 116R, 118R and 120R, respectively. According to this arrangement, light transmitted by the quartz rod 84 is reflected onto a selected one or both of the mirrors 88, 90 by manual rotation of the mirrors within the mirror housing 110. The reflective coatings 116R, 118R and 120R are manually alignable with the light transmitting end portion of the quartz rod 84 for the purpose of selectively directing illumination across the upper mirror 88 only (edge slot 116), across both mirrors 88, 90 (edge slot 118), or across the lower mirror surface 90 only (edge slot 120). By this arrangement, the illumination output of the quartz rod 84 can be directed onto either the upper mirror surface, the lower mirror surface or both mirror surfaces according to the requirements of the procedure being performed.

Although a preferred embodiment of the invention has been described in some detail herein, those skilled in the art will recognize that various substitutions and modifications may be made without departing from the scope and spirit of the invention as defined by the appended claims.

I claim:

1. An intraoral instrument comprising:
   a mirror assembly;
   a tubular extension member coupled to the mirror assembly, the tubular extension member having a longitudinal supply passage;
   a handle coupled to the tubular extension member, said handle including a valve chamber, a first fluid supply conduit, a second fluid supply conduit and an outlet passage, the valve chamber having first and second inlet ports and at least one outlet port;
   the first fluid supply conduit being coupled in flow communication with the first inlet port for conveying a first fluid into the valve chamber, the second fluid supply conduit being coupled in flow communication with the second inlet port for conveying a second fluid into the valve chamber, the outlet passage being coupled in flow communication with the valve chamber outlet port and in flow communication with the longitudinal supply passage of the extension member; and
   a valve member movable in the valve chamber for selectively opening and closing the first and second valve inlet ports.

2. The intraoral instrument of claim 1 wherein said valve member is movable from a first position in which said first and second inlet ports are blocked to a second position in which the first inlet port is coupled in flow communication with said at least one outlet port.

3. The intraoral instrument of claim 1 wherein said valve member is moveable to a third position in which the first and second inlet ports are coupled in flow communication with said at least one outlet port.

4. The intraoral instrument of claim 2 wherein said valve member is movable to a fourth position in which the first inlet port is blocked and the second inlet port is coupled in flow communication with said at least one outlet port.

5. The intraoral instrument of claim 1, wherein the handle is intersected by an annular socket and the extension member including a connector received for rotation within the socket.

6. The intraoral instrument of claim 1, wherein the valve member includes a body member which is radially intersected by an annular groove and by one or more radial bores, and intersected longitudinally by a blind bore.

7. An intraoral instrument comprising:
   a mirror assembly;
   a handle including a supply passage and a suction passage;
   a tubular extension member having a first end portion coupled to the mirror assembly and a second end portion coupled to said handle, the tubular extension member including a first tubular member and a second tubular member disposed within the first tubular member, thereby defining a central flow passage and an annular flow passage, the central flow passage being coupled in flow communication with the supply passage and the annular flow passage being coupled in flow communication with the suction passage.

8. The intraoral instrument of claim 7 further comprising a light transmissive member disposed within the central flow passage.

9. The intraoral instrument of claim 7 wherein the mirror assembly includes at least one slot disposed in flow communication with the central flow passage, and at least one slot disposed in flow communication with the annular flow passage.

10. The intraoral instrument of claim 7, the handle including a valve chamber and a valve element movable in the valve chamber for selectively permitting the flow of air only, air and water, or water only to flow through the supply passage to said mirror assembly.

11. The intraoral instrument of claim 7, the handle being intersected by an annular socket and the tubular extension member including a connector portion mounted for rotation within the socket.

12. An intraoral instrument comprising:
a handle having a supply passage and a suction passage;
a tubular extension member having an end portion coupled to the handle and having at least one flow passage; and,
a mirror assembly coupled to the tubular extension member, the mirror assembly including a housing having a mirror mounted for rotation therein, the mirror having an edge portion and first and second slots formed on the edge portion, the mirror being manually rotatable within the housing from a first position in which the first slot is coupled in flow communication with said at least one flow passage, to a second position in which the second slot is coupled in flow communication with said at least one flow passage.

13. The intraoral instrument of claim 12 wherein the mirror assembly comprises first and second mirrors stacked back-to-back and the first and second slots are formed in peripheral edge portions of the first and second mirrors, respectively.

14. The intraoral instrument of claim 12, including:
a light transmissive member disposed within the tubular extension member; and
first and second light reflective members are disposed within the first and second slots, respectively, for reflecting illumination from the light transmissive member in the first and second mirror positions, respectively.

15. The intraoral instrument of claim 12 further comprising a valve chamber formed in the handle and a valve element movable in the valve chamber for selectively permitting a first fluid or a second fluid to flow through said at least one flow passage.

16. The intraoral instrument of claim 12, wherein:
the handle including an annular socket and the extension member including a connector mounted for rotation within the socket.

17. An intraoral instrument comprising:
a handle including a valve chamber, a first fluid supply conduit, a second fluid supply conduit, a supply passage, and a suction passage, the valve chamber having first and second inlet ports, at least one outlet port, and a valve member movable therein for selectively opening and closing the inlet ports, the first fluid supply conduit being coupled in flow communication with the first inlet port for conveying a first fluid to the valve chamber, the second fluid supply conduit being coupled in flow communication with the second inlet port for conveying a second fluid to the valve chamber, and the supply passage being coupled in flow communication with the at least one valve chamber outlet port;

a tubular extension member coupled to said handle, said tubular extension member including first and second annular flow passages, the first annular flow passage being coupled in flow communication with the supply passage and the second annular flow passage being coupled in flow communication with the suction passage; and, a mirror assembly coupled to the tubular extension member, the mirror assembly including a housing having a mirror mounted therein, the housing having a peripheral edge portion intersected by at least one slot, the at least one slot being coupled in flow communication with the second annular flow passage for conducting suction flow from the mirror.

18. An intraoral instrument comprising:
a handle including a cylindrical body and a tapered end portion, the tapered end portion being rotatably coupled to the cylindrical body, said handle being intersected by a valve chamber, a first fluid supply conduit, a second fluid supply conduit, a supply passage, and a suction passage, the valve chamber having first and second inlet ports, an outlet port, and a valve member disposed for reciprocal movement in the valve chamber, the first fluid supply conduit being coupled in flow communication with the first inlet port for conveying a first fluid to the valve chamber, the second fluid supply conduit being coupled in flow communication with the second inlet port for conveying a second fluid to the valve chamber, the valve member being movable in the valve chamber from a first position in which the first and second inlet ports are blocked to a second position in which the first inlet port is in flow communication with the valve chamber outlet port, to a third position in which the first and second inlet ports are in flow communication with the outlet port, and being movable to a fourth position in which the second inlet port is in flow communication with the outlet port, the supply passage being coupled in flow communication with the valve chamber outlet port, and the suction passage having an outlet port adapted for connection to a suction source;

a lamp disposed within the handle and electrically connected to electrical power conductors;

a tubular extension member coupled to the tapered end of said handle, said tubular extension member including first and second annular flow passages, the first annular flow passage being coupled in flow communication with the supply passage, and the second annular flow passage being coupled in flow communication with the suction passage;

a double-sided mirror assembly coupled to the tubular extension member, the double-sided mirror assembly including a housing and first and second mirrors mounted for rotation therein, the mirrors having edge portions intersected by first and second slots, respectively, the mirrors being rotatable to a first position in which the first slot is coupled in flow communication with the first annular flow passage for discharging at least one fluid onto the first mirror, and being rotatable to a second position in which the second slot is coupled in flow communication with the first annular flow passage for discharging at least one fluid onto the second mirror; and, a light transmissive member disposed within one of the flow passages and having one end proximate the lamp and an opposite end proximate the mirror assembly for conducting light to the mirror assembly.

19. An intraoral instrument comprising:

a handle having a supply passage and a suction passage;

a tubular extension member coupled to the handle, the tubular extension member including first and second flow passages coupled to the supply passage and to the suction passage, respectively; and, a mirror assembly coupled to the tubular extension member, the mirror assembly including a housing and a double-sided mirror mounted therein, edge portions of the double-sided mirror being intersected by first and second slots, the double-sided mirror being manually rotatable within the housing from a first position in which the first slot is coupled in flow communication with the first flow passage, and rotatable to a second position in which the second slot is coupled in flow communication with the first low passage, wherein the first and second slots forming discharge openings that are oriented with respect to the viewing axis of each mirror for discharging water, air or a mixture of air and water transversely across either one or both mirror surfaces in the first and second positions, respectively.

* * * * *

UNITED STATES PATENT AND TRADEMARK OFFICE
CERTIFICATE OF CORRECTION

PATENT NO. : 5,951,284
DATED : Sep. 14, 1999
INVENTOR(S) : James A. Lake

It is certified that error appears in the above-indentified patent and that said Letters Patent is hereby corrected as shown below:

Column 10, Claim 19, Line 10, delete "low" and insert -- flow --.

Signed and Sealed this

Seventh Day of March, 2000

Attest:

Q. TODD DICKINSON

Attesting Officer

Commissioner of Patents and Trademarks